(12) United States Patent
Katouzian

(10) Patent No.: US 11,823,775 B2
(45) Date of Patent: Nov. 21, 2023

(54) HASHING ELECTRONIC RECORDS

(71) Applicant: Merative US L.P., Ann Arbor, MI (US)

(72) Inventor: Amin Katouzian, Lexington, MA (US)

(*) Notice: Subject to any disclaimer, the term of this patent is extended or adjusted under 35 U.S.C. 154(b) by 316 days.

(21) Appl. No.: 17/093,267

(22) Filed: Nov. 9, 2020

(65) Prior Publication Data

US 2022/0148691 A1  May 12, 2022

(51) Int. Cl.
| | | |
|---|---|---|
| *G16H 10/60* | (2018.01) | |
| *G06F 16/13* | (2019.01) | |
| *G16H 50/70* | (2018.01) | |
| *G16H 70/60* | (2018.01) | |
| *G06F 40/30* | (2020.01) | |
| *G06V 30/414* | (2022.01) | |

(52) U.S. Cl.
CPC ........... *G16H 10/60* (2018.01); *G06F 16/137* (2019.01); *G06F 40/30* (2020.01); *G16H 50/70* (2018.01); *G16H 70/60* (2018.01); *G06V 30/414* (2022.01)

(58) Field of Classification Search
CPC ........ G16H 10/60; G16H 50/70; G16H 70/60; G06F 16/137; G06F 40/20; G06V 30/414
See application file for complete search history.

(56) References Cited

U.S. PATENT DOCUMENTS

| | | | |
|---|---|---|---|
| 2006/0218013 A1* | 9/2006 | Nahra | G16H 10/60 |
| | | | 707/999.102 |
| 2017/0249481 A1* | 8/2017 | Edison | H04L 63/083 |
| 2018/0246985 A1 | 8/2018 | Sclaroff et al. | |
| 2019/0221304 A1* | 7/2019 | Ionasec | G06F 40/20 |
| 2021/0098091 A1* | 4/2021 | Gomes | G16H 10/60 |
| 2021/0098092 A1* | 4/2021 | Katuwal | G06F 16/152 |
| 2021/0240853 A1* | 8/2021 | Carlson | G16H 10/20 |

OTHER PUBLICATIONS

Lee et al. Privacy-Preserving Patient Similarity Learning in a Federated Environment: Development and Analysis (Year: 2018).*
Mell et al., "The NIST Definition of Cloud Computing," Recommendations of the National Institute of Standards and Technology, U.S. Department of Commerce, Special Publication 800-145, Sep. 2011, 7 pgs.
Robinson et al., "Fast and simple comparison of semi-structured data, with emphasis on electronic health records," bioRxiv (2018): 293183, 13 pages.

* cited by examiner

*Primary Examiner* — Jonathan Ng
(74) *Attorney, Agent, or Firm* — Stephen J. Walder, Jr.

(57) ABSTRACT

Provided is a method, computer program product, and system for hashing electronic health records. A processor may collect a set of electronic health records (EHRs). The processor may perform an encounter analysis on the set of EHRs to determine a set of attributes associated to the set of EHRs. The processor may hash the set of attributes to generate one or more hashing indexes that correspond to the set of EHRs. The processor may store the one or more hashing indexes in a list used for document retrieval.

17 Claims, 11 Drawing Sheets

HASHING ELECTRONIC RECORDS

BACKGROUND

The present disclosure relates generally to the field of computing and, more specifically, to hashing electronic health records (EHRs) to improve decision making related to patient care.

With the advent of computers, most healthcare facilities (e.g., hospitals, doctor's offices, rehabilitation facilities, etc.) have moved from tracking and/or documenting a patient's health records using paper systems to electronic systems that utilize EHRs.

SUMMARY

Embodiments of the present disclosure include a method, computer program product, and system for hashing electronic health records. A processor may collect a set of electronic health records (EHRs). The processor may perform an encounter analysis on the set of EHRs to determine a set of attributes associated to the set of EHRs. The processor may hash the set of attributes to generate one or more hashing indexes that correspond to the set of EHRs. The processor may store the one or more hashing indexes in a list used for document retrieval.

The above summary is not intended to describe each illustrated embodiment or every implementation of the present disclosure.

BRIEF DESCRIPTION OF THE DRAWINGS

The drawings included in the present disclosure are incorporated into, and form part of, the specification. They illustrate embodiments of the present disclosure and, along with the description, serve to explain the principles of the disclosure. The drawings are only illustrative of typical embodiments and do not limit the disclosure.

Figure 1:
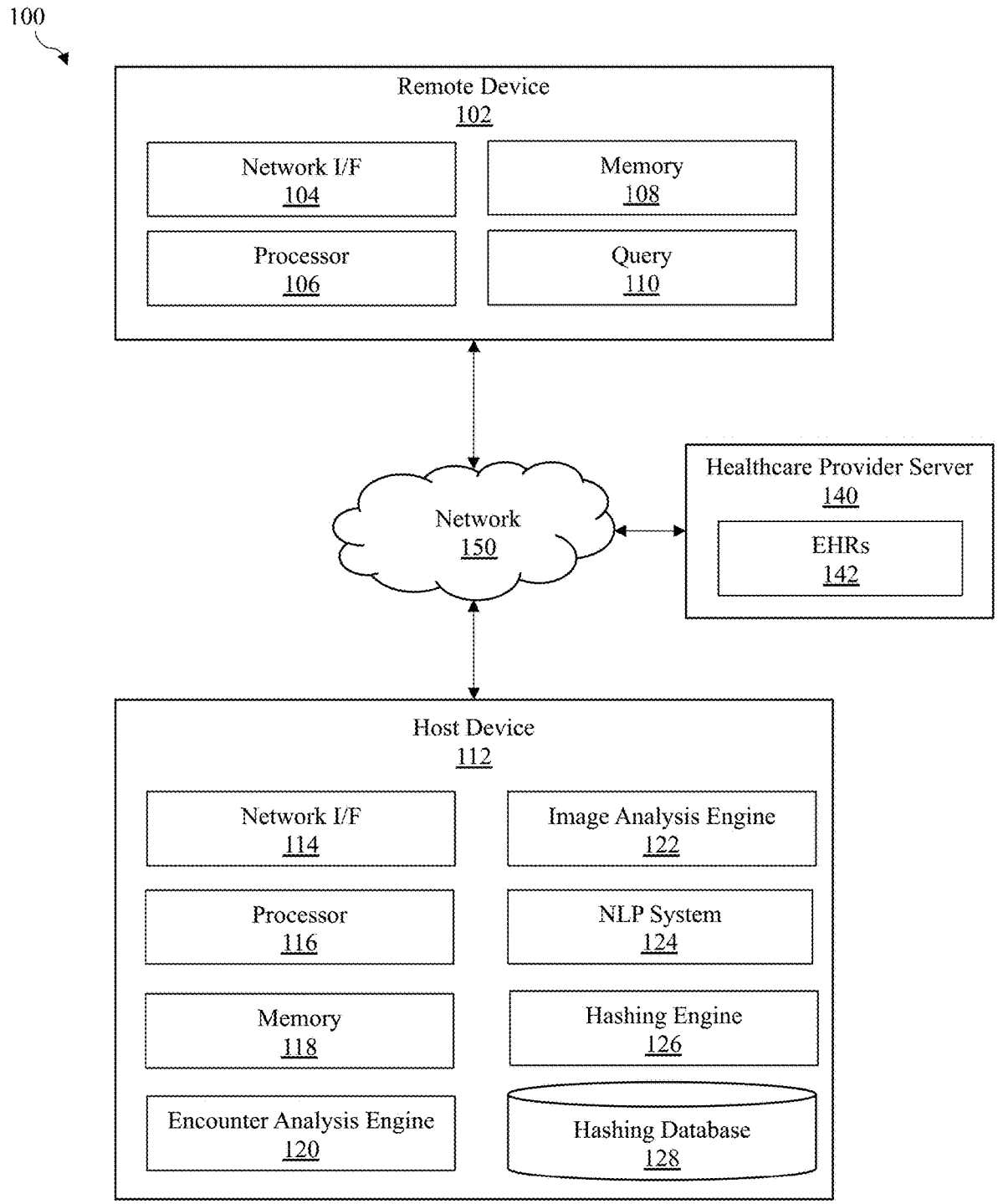
FIG. 1 illustrates a block diagram of an example system in which illustrative embodiments of the present disclosure may be implemented.

While the embodiments described herein are amenable to various modifications and alternative forms, specifics thereof have been shown by way of example in the drawings and will be described in detail. It should be understood, however, that the particular embodiments described are not to be taken in a limiting sense. On the contrary, the intention is to cover all modifications, equivalents, and alternatives falling within the spirit and scope of the disclosure.

DETAILED DESCRIPTION

Aspects of the present disclosure relate to the field of computing and, more particularly, to hashing electronic health records (EHRs) to improve decision making related to patient care. While the present disclosure is not necessarily limited to such applications, various attributes of the disclosure may be appreciated through a discussion of various examples using this context.

With the advent of computers, most healthcare facilities (e.g., hospitals, doctor's offices, rehabilitation facilities, etc.) have moved from tracking and/or documenting a patient's health records using paper systems to electronic systems that utilize EHRs. In many instances, healthcare providers (e.g., a doctor, physician, physical therapist, etc.) may use available EHRs from other patients when making decisions on treatment for a current patient. For example, a doctor may analyze medical records of previous patients that have similar medical issues to a current patient. Using the EHRs of the similar patients, the doctor can make an informed decision based on what kind of medical treatment has been successful for similar patients in the past.

However, current retrieval systems for collecting EHRs for decision making purposes may be inefficient. For example, current retrieval systems may require a healthcare provider to enter various search terms to identify a particular disease or treatment plan for a specific type of patient (e.g., based on demographic, symptoms, medications, history, etc.) from a healthcare database. However, the retrieved records from the search may include vast amounts of irrelevant information if the search terms are not specifically tailored to the patient's care. This may result in a healthcare provider wasting time trying to enter accurate search terms in an attempt to gather relevant information that may be used to make a properly informed patient care decision.

Embodiments of the present disclosure relate to a method, computer program product, and system for hashing electronic health records (EHRs) to provide cross-document based reasoning for making decisions related to a patient's care. Using a hashing function or hashing technique on the collected EHRs allows the system to quickly retrieve any relevant medical/health data related to similar patients when providing various diagnoses for a patient. Typically, EHR data is represented in high dimensional feature spaces (e.g., in order of thousands of dimensions), which may be difficult and/or timely to traverse. Providing hashing values for various attributes/features extracted from the EHRs allows for the generation of a hashing index that increases the speed of retrieval of relevant health data. Once retrieved, this health data may be used to support the decision-making process by basing patient care decisions on actual evidence of similar patients gathered from EHRs.

In embodiments, the system may collect EHRs for a plurality of patients (e.g. past/current patients). The EHRs may be accessible through a healthcare provider (e.g., accessed and/or stored a healthcare provider's server) or healthcare provider's network. The EHRs may include any type of health and/or medical record data (e.g., demographics, medical records number (MRN), medications, patient history, measurements, symptoms, medical diagnosis, modality, vitals, imaging, and the like) associated with the patients.

In embodiments, the system may perform an encounter analysis on the set of EHRs to determine a set of attributes associated with the EHRs. For example, the set of attributes may be determined at each encounter taken from a given patient's EHR, where an encounter is defined as any type of medical consultation or visit with a healthcare provider. For example, an encounter may be a doctor's appointment, medical treatment, lab test, surgery, emergency room visit, pharmacy visit, and the like. Each EHR may include one or more encounters between a respective patient and one or more healthcare providers, where each encounter may comprise multiple attributes. For example, a doctor's appointment may include various attributes such as demographic information, medical history, and or diagnosis provided to a patient during the encounter.

In embodiments, the set of attributes may be determined by performing various feature extraction techniques on the EHRs for the given encounter. For example, using natural language processing (NLP) and/or natural language understanding (NLU), the system may analyze unstructured text extracted from the EHRs to identify that a patient is suffering from a rare medical condition and their doctor has offered a medical opinion for treatment using a non-aggressive medicine.

In another example, the system may use image analysis (e.g., image recognition, feature vector extraction, etc.) to extract various features from medical imaging data that may be used to determine the various attributes related to the EHRs. The medical imaging data may include any type of image used to acquire structural or function images of the body, such as radiography (e.g., X-rays), ultrasound, nuclear medicine, computed tomography (CT), magnetic resonance imaging (MM), and visible light. For example, the system may perform image analysis to extract features from an X-ray of a patient's arm that indicates it is fractured.

In embodiments, the system uses the set of attributes to generate a feature vector (or feature space) to identify informative features from the EHRs. For example, the system may use the set of attributes related to an encounter to generate a feature vector for the specific type of encounter (e.g., gallbladder surgery or chemotherapy treatment). In some embodiments, a feature vector for each encounter may be assigned a label. The label may be any type of label used to describe the encounter and/or features of the encounter. In some embodiments, the label may correspond to an International Classification of Diseases (ICD) code.

In embodiments, the system performs a hashing function on the determined set of attributes to generate one or more hashing indexes that correspond to the set of EHRs. In embodiments, the hashing indexes may be stored in a list used for document retrieval. In embodiments, the system generates hash values for the attributes by applying one or more hash functions to the set of attributes. In some embodiments, the set of attributes may be hashed according to any type of classification and/or characterization technique. For example, the set of attributes may be hashed according to an encounter, a modality, a clinical outcome, a demographic, a symptom, a location, a medication, intra-level aggregation, and/or inter-level aggregation. It is noted that this list is not meant to be limiting and that other classifications of the attributes may be performed.

In some embodiments, hash values may be generated for individual attributes or aggregated attributes. For example, two or more aggregated attributes may be encoded with a single hash value. Using the hash values, the system may generate one or more hashing indexes that may be used to sort and/or retrieve various attributes related to the EHRs.

In embodiments, the system may receive a request (or query) to retrieve one or more similar attributes that match a specific attribute of the request. The system may analyze the request to determine the specific attribute using NLP. For example, a healthcare provider may request to see any medical records data related to treating heart disease for a specific demographic of patients. The system will identify heart disease and the given demographic as specific attributes and search the hashing indexes for similar attributes that match the request.

In some embodiments, identifying similar attributes from the hashing index that match the specific attribute from the request may be performed by computing a pairwise distance (e.g., Hamming distance) between the specific attribute from the query and the individually encoded attributes from the set of attributes determined from the EHRs. In embodiments, the system may compare the distance between the specific attribute and each of the set of attributes to a distance threshold. Once the distances of the set of attributes are computed and compared, the system will retrieve only the one or more similar encounter attributes that meet the distance threshold. For example, the system will identify similar patients to the specific demographic that have suffered from heart disease using the hashing index/values.

In some embodiments, the system may output the retrieved one or more similar attributes to a user. For example, the one or more similar attributes may be sent to the remote device in response to the query. In some embodiments, the retrieved one or more similar attributes sent to the user may be classified by type (e.g., encounter, modality, inter-level aggregation, intra-level aggregation). In this way, the user may leverage any relevant information associated with the similar attributes to aid in making informed decisions regarding a current patient's care.

In some embodiments, the respective steps of collecting EHRs, performing encounter analysis on the EHRs, and hashing the set of attributes determined from the EHRs may be performed automatically by using machine learning. The term "machine-learning"—and based on that the term "machine-learning model"—may denote known methods of enabling a computer system to improve its capabilities automatically through experience and/or repetition without procedural programming. Thereby, machine-learning can be seen as a subset of artificial intelligence. Machine-learning algorithms build a mathematical model—i.e., the machine-learning model—based on sample data, known as "training data", in order to make predictions or decisions without being explicitly programmed to do so.

In embodiments, the patient(s) must opt into the system in order for the system to collect their information (e.g., EHRs), and the patient may determine which other users (e.g., healthcare provider(s), doctors, etc.) can utilize the collected data. For example, during an initialization process, the system may inform the patient of the types of data that it will collect (e.g., medical conditions, EHRs, treatment plans, etc.) and the reasons why the data is being collected. In these embodiments, the system will only start collecting the patient information upon the patient explicitly permitting the collection. Furthermore, the system may only collect the data that is necessary for aiding in the decision-making process when providing patient care by an identified healthcare provider. The collected data may be anonymized and/or encrypted while in use, and the data may only be maintained as needed for aiding in decision making. If a patient chooses to opt out of the system, any patient information previously collected may be permanently deleted.

The aforementioned advantages are example advantages, and not all advantages are discussed. Furthermore, embodiments of the present disclosure can exist that contain all, some, or none of the aforementioned advantages while remaining within the spirit and scope of the present disclosure.

Turning now to the figures, FIG. 1 illustrates a block diagram of an example system 100 in which illustrative embodiments of the present disclosure may be implemented. In some embodiments, the system 100 may include a remote device 102, a host device 112, and a healthcare provider server 140.

Consistent with various embodiments, the remote device 102, the host device 112, and the healthcare provider server 140 may be computer systems. In some embodiments, the remote device 102, the host device 112, and the healthcare provider server 140 may be substantially similar to computer system 1101 of FIG. 8. In the illustrated embodiment, the remote device 102 and the host device 112 may include one or more processors 106 and 116 and one or more memories 108 and 118, respectively. The remote device 102 and the host device 112 may be configured to communicate with each other through an internal or external network interface 104 and 114. The network interfaces 104 and 114 may be, e.g., modems or network interface cards. The remote device 102 and/or the host device 112 may be equipped with a display or monitor. Additionally, the remote device 102 and/or the host device 112 may include optional input devices (e.g., a keyboard, mouse, scanner, or other input device), and/or any commercially available or custom software (e.g., browser software, communications software, server software, natural language processing software, search engine and/or web crawling software, filter modules for filtering content based upon predefined parameters, etc.). The host device 112 may, in various embodiments, be connected to an output device. For example, the output device may be a tablet, an e-reader, or a printer. In some embodiments, the remote device 102 and/or the host device 112 may be servers, desktops, laptops, or hand-held devices. In some embodiments, the host device 112 may be configured as a virtual machine that is accessible by the remote device 102 over network 150. In embodiments, the healthcare provider server 140 may also contain similar components (e.g., processors, memories, network I/F) as the remote device 102 and the host device 112, however, for brevity purposes these components are not shown.

The remote device 102, the host device 112, and the healthcare provider server 140 may be distant from each other and communicate over a network 150. In some embodiments, the host device 112 may be a central hub from which remote device 102 and the healthcare provider server 140 can establish a communication connection, such as in a client-server networking model. Alternatively, the host device 112, the healthcare provider server 140, and the remote device 102 may be configured in any other suitable networking relationship (e.g., in a peer-to-peer configuration or using any other network topology).

In some embodiments, the network 150 can be implemented using any number of any suitable communications media. For example, the network 150 may be a wide area network (WAN), a local area network (LAN), an internet, or an intranet. In certain embodiments, the remote device 102, the host device 112, and the healthcare provider server 140 may be local to each other, and communicate via any appropriate local communication medium. For example, the remote device 102, the host device 112, and the healthcare provider server 140 may communicate using a local area network (LAN), one or more hardwire connections, a wireless link or router, or an intranet. In some embodiments, the remote device 102, the host device 112, and the healthcare provider server 140 may be communicatively coupled using a combination of one or more networks and/or one or more local connections. For example, the remote device 102 may be hardwired to the host device 112 (e.g., connected with an Ethernet cable) while the healthcare provider server 140 may communicate with the host device using the network 150 (e.g., over the Internet).

In some embodiments, the network 150 can be implemented within a cloud computing environment, or using one or more cloud computing services. Consistent with various embodiments, a cloud computing environment may include a network-based, distributed data processing system that provides one or more cloud computing services. Further, a cloud computing environment may include many computers (e.g., hundreds or thousands of computers or more) disposed within one or more data centers and configured to share resources over the network 150. In embodiments, network 150 may be substantially similar cloud computing environment 50 illustrated in FIG. 9.

In the illustrated embodiment, the host device 112 further includes encounter analysis engine 120, image analysis engine 122, natural language processing (NLP) system 124, hashing engine 126, and database 128.

In embodiments, the host device 112 is configured to collect, gather, and/or analyze EHRs 142 received from the healthcare provider server 140. The EHRs 142 may comprise any type of health and/or medical record data (e.g., demographics, medications, patient history, measurements, symptoms, medical diagnosis, vitals, and the like) associated with one or more patients. In embodiments, the encounter analysis engine 120 performs an encounter analysis on the collected EHRs 142. The encounter analysis engine 120 is configured to analyze the EHRs 142 and determine a set of attributes associated with the EHRs. For example, the attributes may be any type of health data or feature that is specific to the EHR.

In embodiments, the NLP system 124 is configured extract specific features from unstructured textual data collected from the EHRs 142 in order to determine the set of attributes. For example, the NLP system 124 may extract text from medical records for various patients indicating types of treatment plans, medications, and our outcomes of resulting from the treatment plans. In embodiments, the NLP system 124 may include a natural language processor having numerous subcomponents, such as a tokenizer, a part-of-speech (POS) tagger, a semantic relationship identifier, and a syntactic relationship identifier. An example natural language processing system is discussed in more detail in reference to FIG. 2.

In embodiments, the image analysis engine 122 is configured to extract specific features from medical imaging data collected from the EHRs 142 to determine the set of attributes. The medical imaging data may include any type of image used to acquire structural or function images of the body, such as radiography (e.g., X-rays), ultrasound, nuclear medicine, computed tomography (CT) scans, magnetic resonance imaging (MRI), and visible light.

In embodiments, the hashing engine 126 is configured to perform hashing functions that encode the set of attributes determined from the EHRs 142 with one or more hashing values. The hashing engine 126 may generate a hashing index that may be used to retrieve EHRs related to the set of hashed attributes. The hashing index may be stored in hashing database 128.

In embodiments, the remote device 102 may enable users to submit a query 110 to the host device 112 requesting retrieval of relevant EHR data via the hashing index. In embodiments, the query 110 may be in the form of unstructured text entered in a user interface (UI), and the UI may be any type of interface (e.g., command line prompts, menu screens, graphical user interfaces). The UI may allow a user to interact with the remote device 102 to submit the query 110 to the host device 112.

In embodiments, the host device 112 may use a machine learning to improve its capabilities automatically through training, experience, and/or repetition without procedural programming. For example, the host device 112 may use machine learning to analyze the accuracy of the hashing values respective to the identified given attributes. If determinations are made that the hashing value(s) corresponds to an incorrect attribute(s), the host device 112 may modify machine learning algorithms for hashing the attributes accordingly. In this way, the system may become more accurate in retrieving accurate/relevant medical data in response to a request or query to produce medical data for making decisions regarding patient care.

Machine learning algorithms can include, but are not limited to, decision tree learning (e.g., random forest), association rule learning, artificial neural networks, deep learning, inductive logic programming, support vector machines, clustering, Bayesian networks, reinforcement learning, representation learning, similarity/metric training, sparse dictionary learning, genetic algorithms, rule-based learning, and/or other machine learning techniques.

For example, the machine learning algorithms can utilize one or more of the following example techniques: K-nearest neighbor (KNN), learning vector quantization (LVQ), self-organizing map (SOM), logistic regression, ordinary least squares regression (OLSR), linear regression, stepwise regression, multivariate adaptive regression spline (MARS), ridge regression, least absolute shrinkage and selection operator (LASSO), elastic net, least-angle regression (LARS), probabilistic classifier, naïve Bayes classifier, binary classifier, linear classifier, hierarchical classifier, canonical correlation analysis (CCA), factor analysis, independent component analysis (ICA), linear discriminant analysis (LDA), multidimensional scaling (MDS), non-negative metric factorization (NMF), partial least squares regression (PLSR), principal component analysis (PCA), principal component regression (PCR), Sammon mapping, t-distributed stochastic neighbor embedding (t-SNE), bootstrap aggregating, ensemble averaging, gradient boosted decision tree (GBDT), gradient boosting machine (GBM), inductive bias algorithms, Q-learning, state-action-reward-state-action (SARSA), temporal difference (TD) learning, apriori algorithms, equivalence class transformation (ECLAT) algorithms, Gaussian process regression, gene expression programming, group method of data handling (GMDH), inductive logic programming, instance-based learning, logistic model trees, information fuzzy networks (IFN), hidden Markov models, Gaussian naïve Bayes, multinomial naïve Bayes, averaged one-dependence estimators (AODE), Bayesian network (BN), classification and regression tree (CART), chi-squared automatic interaction detection (CHAID), expectation-maximization algorithm, feed-forward neural networks, logic learning machine, self-organizing map, single-linkage clustering, fuzzy clustering, hierarchical clustering, Boltzmann machines, convolutional neural networks, recurrent neural networks, hierarchical temporal memory (HTM), and/or other machine learning techniques.

While FIG. 1 illustrates an example system 100 with a single remote device 102, a single host device 112, and a single healthcare provider server 140, suitable computing environments for implementing embodiments of this disclosure may include any number of remote devices, host devices, and healthcare provider servers. The various modules, systems, and components illustrated in FIG. 1 may exist, if at all, across a plurality of remote devices, host devices, and healthcare provider servers.

It is noted that FIG. 1 is intended to depict the representative major components of an exemplary system 100. In some embodiments, however, individual components may have greater or lesser complexity than as represented in FIG. 1, components other than or in addition to those shown in FIG. 1 may be present, and the number, type, and configuration of such components may vary.

Figure 2:
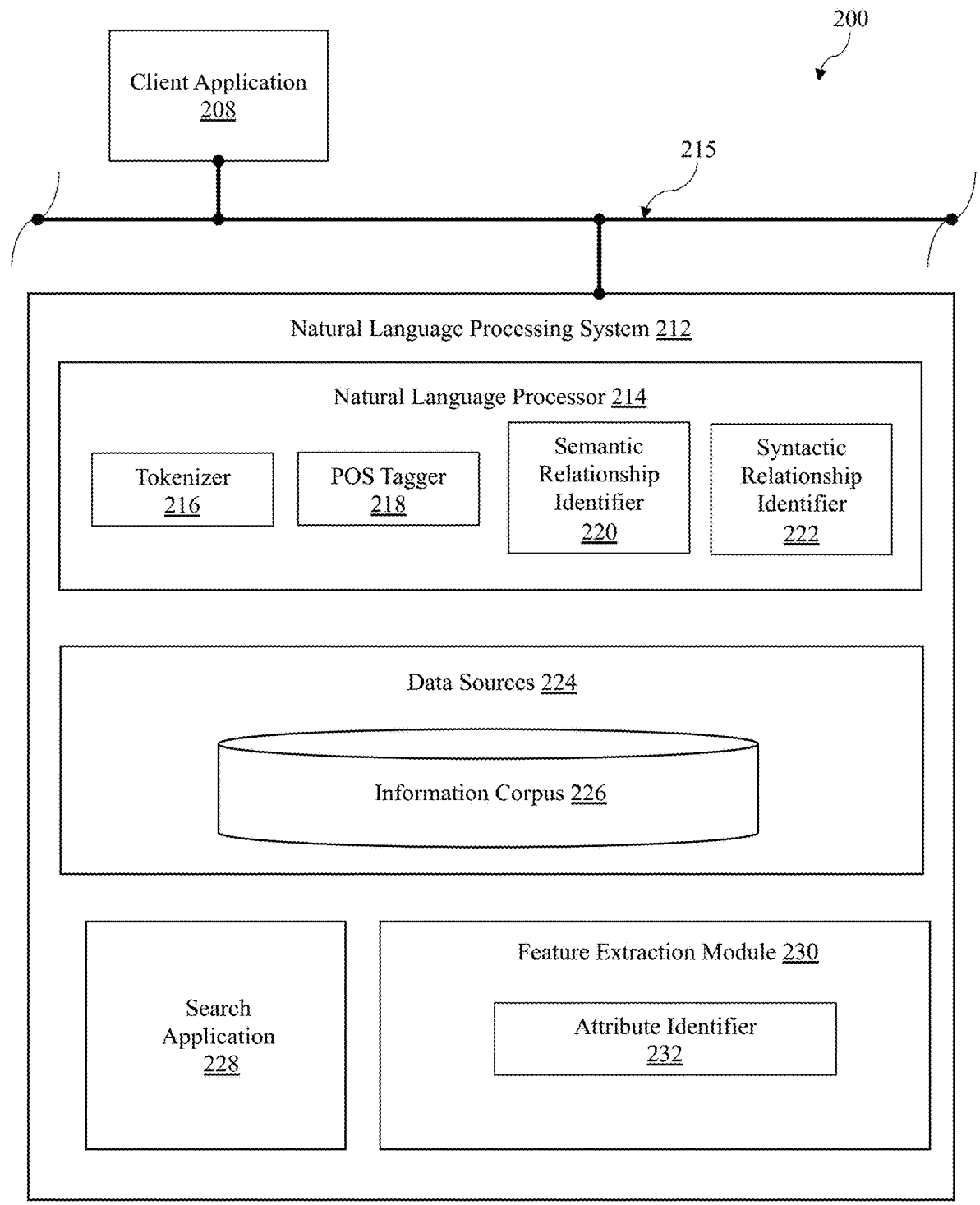
FIG. 2 illustrates a block diagram of an example natural language processing system configured to extract features from electronic health records, in accordance with embodiments of the present disclosure.

Referring now to FIG. 2, shown is a block diagram of an exemplary system architecture 200, including a natural language processing system 212, configured to extract features from electronic health records EHRs, in accordance with embodiments of the present disclosure. In some embodiments, the natural language processing system 212 may include a natural language processor 214, data sources 224, a search application 228, and a feature extraction module 230. The natural language processor 214 may be a computer module that analyzes the collected/received EHRs 142 from the healthcare provider server 140. In some embodiment, the EHRs comprise unstructured data (e.g., medical history, prescriptions, diagnoses, treatment plans, etc.) related to various health and/or medical records of one or more patients. The natural language processor 214 may perform various methods and techniques for analyzing the EHRs 142 (e.g., syntactic analysis, semantic analysis, etc.). The natural language processor 214 may be configured to recognize and analyze any number of natural languages. In some embodiments, the natural language processor 214 may parse passages of the EHRs 142. Further, the natural language processor 214 may include various modules to perform analyses of the EHRs 142. These modules may include, but are not limited to, a tokenizer 216, a part-of-speech (POS) tagger 218, a semantic relationship identifier 220, and a syntactic relationship identifier 222.

In some embodiments, the tokenizer 216 may be a computer module that performs lexical analysis. The tokenizer 216 may convert a sequence of characters into a sequence of tokens. A token may be a string of characters included in an EHR and categorized as a meaningful symbol. Further, in some embodiments, the tokenizer 216 may identify word boundaries in an EHR and break any text passages within the EHR into their component text elements, such as words, multiword tokens, numbers, and punctuation marks. In some embodiments, the tokenizer 216 may receive a string of characters, identify the lexemes in the string, and categorize them into tokens.

Consistent with various embodiments, the POS tagger 218 may be a computer module that marks up a word in passages to correspond to a particular part of speech. The POS tagger 218 may read a passage or other text in natural language and assign a part of speech to each word or other token. The POS tagger 218 may determine the part of speech to which a word (or other text element) corresponds based on the definition of the word and the context of the word. The context of a word may be based on its relationship with adjacent and related words in a phrase, sentence, or paragraph. In some embodiments, the context of a word may be dependent on one or more previously analyzed EHRs (e.g., the content of a first encounter related to a patient may shed light on the meaning of text elements in a second encounter related to the same patient, particularly if they are part of the same corpus or universe). Examples of parts of speech that may be assigned to words include, but are not limited to, nouns, verbs, adjectives, adverbs, and the like. Examples of other part of speech categories that POS tagger 218 may assign include, but are not limited to, comparative or superlative adverbs, wh-adverbs, conjunctions, determiners, negative particles, possessive markers, prepositions, wh-pronouns, and the like. In some embodiments, the POS tagger 218 may tag or otherwise annotate tokens of a passage with part of speech categories. In some embodiments, the POS tagger 218 may tag tokens or words of a passage to be parsed by the natural language processing system 212.

In some embodiments, the semantic relationship identifier 220 may be a computer module that may be configured to identify semantic relationships of recognized text elements (e.g., words, phrases) in the EHRs 142. In some embodiments, the semantic relationship identifier 220 may determine functional dependencies between entities and other semantic relationships.

Consistent with various embodiments, the syntactic relationship identifier 222 may be a computer module that may be configured to identify syntactic relationships in a passage composed of tokens. The syntactic relationship identifier 222 may determine the grammatical structure of sentences such as, for example, which groups of words are associated as phrases and which word is the subject or object of a verb. The syntactic relationship identifier 222 may conform to formal grammar.

In some embodiments, the natural language processor 214 may be a computer module that may parse an EHR and generate corresponding data structures for one or more portions of the EHR. For example, the natural language processor 214 may output parsed text elements from an EHR that may be used to generate a label or classification of an encounter associated with the EHR. In some embodiments, a parsed text element may be represented in the form of a parse tree or other graph structure. To generate the parsed text element, the natural language processor 214 may trigger computer modules 216-222.

In some embodiments, the output of the natural language processor 214 may be stored as an information corpus 226 in one or more data sources 224. In some embodiments, data sources 224 may include data warehouses, information corpora, data models, and document repositories that are associated with the EHR 142. In some embodiments, data sources 224 may be located on healthcare provider server 140. The information corpus 226 may enable data storage and retrieval. In some embodiments, the information corpus 226 may be a storage mechanism that houses a standardized, consistent, clean, and integrated copy of the ingested and parsed EHR 142 used to generate one or more feature vectors. The information corpus 226 may also include a list of concepts found in the ingested EHR used to respond to the query 110 received from remote device 102. The data may be sourced from various operational systems. Data stored in the information corpus 226 may be structured in a way to specifically address analytic requirements. In some embodiments, the information corpus 226 may be a relational database.

In some embodiments, the natural language processing system 212 may include a feature extraction module 230. The feature extraction module 230 may be a computer module that is configured to extract features from the ingested and analyzed EHRs 142. In some embodiments, the feature extraction module 230 may contain one or more submodules. For example, the feature extraction module 230 may contain an encounter attribute identifier 232 that may be configured to identify one or more encounter attributes from the extracted feature of the EHRs.

In some embodiments, a remote device (such as remote device 102 of FIG. 1) may submit a query 110 to be analyzed by the natural language processing system 212. Such a remote device may include a client application 208, which may be used to send the query 110 via network 215. In some embodiments, the search application 228 may be configured to search one or more databases or other computer systems for content (e.g., EHRs, encounters, modalities, encounter attributes) that is related to the query 110 submitted by a remote device 102. For example, the search application 126 may be configured to search the hashing database 128 to find encounter attributes that are similar to a specific encounter or encounter attribute associated with the submitted query 110. The extracted features or encounter attributes may be stored in a memory (e.g., memory 118, hashing database 128) for determining similarities between the specific encounter attribute related to the query 110 and/or future queries.

In some embodiments, the host device 112 may automatically/continually collect and analyze the EHR 142 (e.g., new health records, unanalyzed documents, etc.) using the natural language processing system 212 to increase the breadth of the hashing database 128. For example, the host device 112 will continually parse new EHRs to determine new attributes for health data and/or features related to one or more patients, relationships between various encounters, modalities, levels, past attributes, and/or characteristics.

Figure 3:
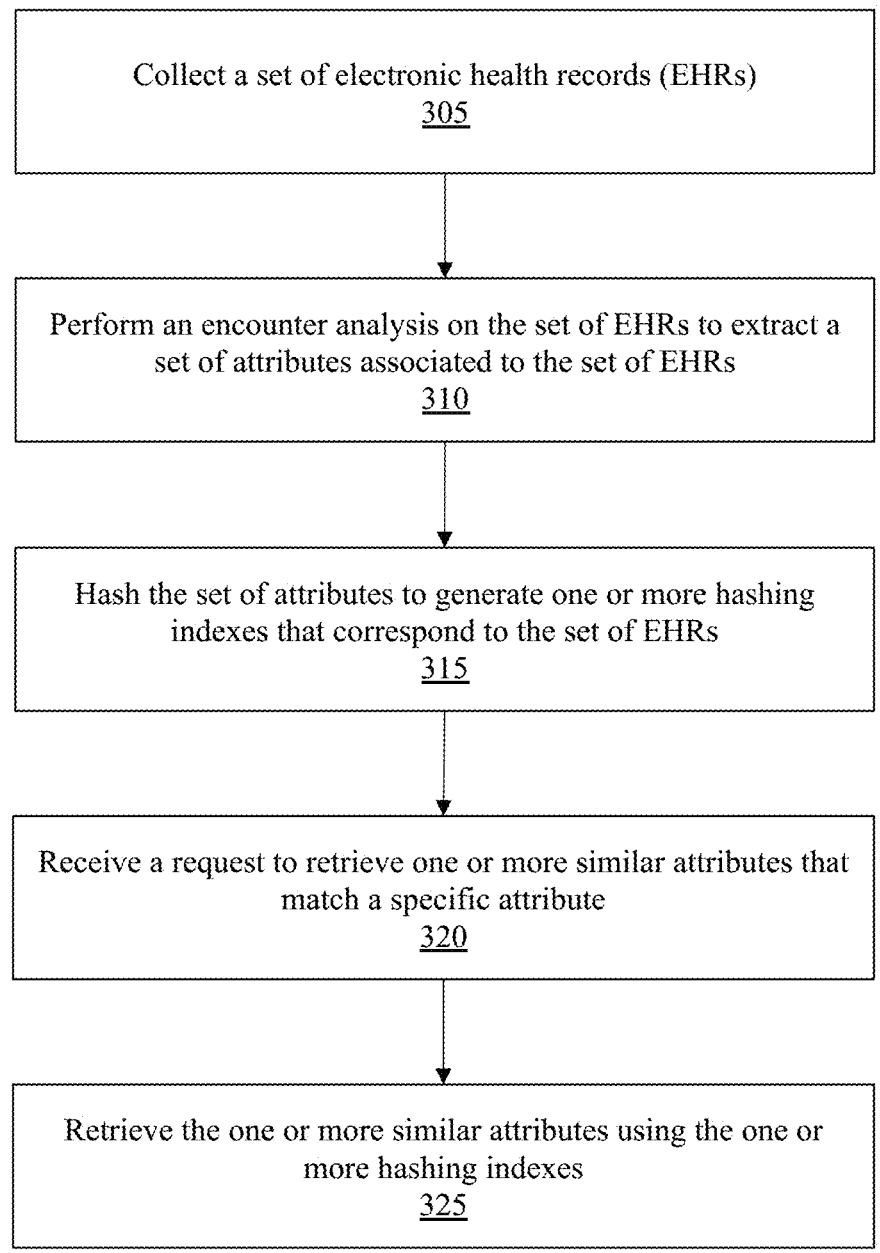
FIG. 3 illustrates a flow diagram of an example process for hashing a set of electronic health records, in accordance with embodiments of the present disclosure.

Referring now to FIG. 3, shown is a flow diagram of an example process 300 for hashing a set of electronic health records, in accordance with embodiments of the present disclosure. The process 300 may be performed by processing logic that comprises hardware (e.g., circuitry, dedicated logic, programmable logic, microcode, etc.), software (e.g., instructions run on a processor), firmware, or a combination thereof. In some embodiments, the process 300 is a computer-implemented process. The process 300 may be performed by processor 116 of FIG. 1.

The process 300 begins by collecting a set of electronic health records (EHRs). This is illustrated at step 305. In embodiments, the EHRs may include any type of health and/or medical record data (e.g., demographics, medical records number (MRN), medications, patient history, measurements, symptoms, medical diagnosis, modality, vitals, imaging, modality, and the like) associated with one or more patients.

The process 300 continues by performing an encounter analysis on the set of EHRs to determine a set of attributes associated with each of the EHRs. This is illustrated at step 310. The set of attributes may be determined by performing various feature extraction techniques on the EHRs. For example, the system may utilize NLP to analyze unstructured textual data from the EHRs to extract features that may be used to determine the various attributes of the EHRs. In some embodiments, the encounter analysis may be performed on the EHRs at various levels to extract the set of attributes. For example, the set of attributes may be determined at each encounter taken from a given patient's EHR, where an encounter is defined as any type of medical consultation or visit with a healthcare provider. For example, an encounter may be a doctor's appointment, medical treatment, lab test, surgery, emergency room visit, pharmacy visit, and the like. Each EHR may include one or more encounters between a respective patient and one or more healthcare providers, where each encounter may comprise multiple attributes. For example, a doctor's appointment may include various attributes such as demographic information, medical history, and or diagnosis provided to a patient during the encounter.

In some embodiments, the system may use image analysis (e.g., image recognition, feature vector extraction, etc.) to extract various features from medical imaging data that may be used to determine the various attributes related to the EHR. For example, the system may perform image analysis to extract features from an MM of a patient's knee that indicates a torn ligament. In another example, the system may extract features from a CT scan that indicates a patient shows signs of heart disease.

In some embodiments, the attributes determined from each encounter may be further classified by type. For example, the modality (e.g., medical diagnosis) provided by the healthcare provider to the patient may be extracted from the EHRs and used to further classify the attributes into subgroups. For example, a modality may include any way in which a disease or illness was diagnosed by the doctor (e.g., a medical diagnosis provided by the doctor using X-ray imaging, a chemotherapy treatment plan, medication schedule, etc.). In some embodiments, the modality may be a subgroup of the encounter.

In some embodiments, the system uses the set of attributes to generate a feature vector (or feature space) to extract informative features from the EHRs. For example, the system may use the set of attributes related to an encounter to generate a feature vector. In some embodiments, a feature vector for each encounter may be assigned a label. The label may be any type of label used to describe the encounter and/or features of the encounter. In some embodiments, the label may correspond to an International Classification of Diseases (ICD) code. For example, based on the given attributes for the encounter (e.g., modality, demographic info, medication, medical history, etc.) the system may assign an ICD code to the encounter. For example, an encounter for a patient that includes attributes indicating chest pain, chest tightness, and shortness of breath may be assigned the ICD code associated with heart disease.

The process 300 continues by hashing the set of attributes to generate one or more hashing indexes that correspond to the set of EHRs. This is illustrated at step 315. In embodiments, the system may store the one or more hashing indexes in a list used for document retrieval. In embodiments, the system generates hash values for the attributes by applying one or more hash functions to the set of attributes. In some embodiments, the set of attributes may be hashed according to any type of classification and/or characterization technique. For example, the set of attributes may be hashed according to an encounter, a modality, a clinical outcome, a demographic, a symptom, a location, a medication, intra-level aggregation of attributes, and/or inter-level aggregation of attributes. It is noted that this list is not meant to be limiting and that other classifications of the attributes may be performed.

In some embodiments, hash values may be generated for individual attributes or aggregated attributes. For example, two or more attributes may be encoded with a single hash value. In some embodiments, this may be done if the two or more attributes are related. For example, a medical disease and a medication used to treat that disease may be encoded with a single hash value since they will often be found in combination. Using the hash values, the system may generate one or more hashing indexes that may be used to sort and/or retrieve various attributes related to the EHRs. In this way, the hashing may be performed to classify the EHRs in various ways. For example, the hash values may be used to classify the EHRs by encounter, which may include more than one attribute, or modality, which may be specific to single attribute (e.g., specific diagnosis). As such, the system may generate one set of indexes to classify the EHRs by encounter, and a second set of indexes to classify the EHRs by modality. In some embodiment, the hash values may be generated at an inter-level aggregation (e.g., between two different types of attributes) and/or intra-level aggregation (e.g., between sub-groups of the attribute).

The process 300 continues by receiving a request to retrieve one or more similar attributes that match a specific attribute. This is illustrated at step 320. In some embodiments, the request may be in the form of a query (e.g., query 110) received from a remote device (e.g., remote device 102). The system may analyze the request to determine the specific attribute using NLP. For example, a user may send a query to the system with a request for medical records data showing treatment for similar patients that have a rare form of cancer as a current patient. The system may identify the rare form of cancer as the specific attribute. In embodiments, one or more specific attributes may be identified from the request (e.g., type of patient, demographic, treatment, modality, etc.).

The process 300 continues by retrieving the one or more similar attributes using the one or more hashing indexes. This is illustrated at step 325. Returning to the previous example, using the hashing indexes, the system may identify/retrieve records for 5 patients that have/had a similar form of the rare cancer, the patients' respective treatments, and the outcomes resulting from the treatments. Using the hashing values from the indexes, the one or more similar attributes (e.g., the medical records data) may be further broken-down or classified by type (e.g., encounter, modality, inter-level or intra-level aggregation). This may be done by hashing the attribute(s) extracted from the query and comparing the resulting hash value(s) to the hash values stored in a hash index. Returning to the previous example, using the hashing index/values, the results may be classified by modality, showing that 2 of the patients were treated with radiation therapy, while 3 patients were treated with chemotherapy. In another example, the hashing index may be used to classify which patients had successful treatment and which patients did not.

In some embodiments, to identify the one or more similar attributes, the system may compute a distance between the specific encounter attribute from the request/query and each of the set of encounter attributes from the one or more hashing indexes. In embodiments, this may be performed by computing a pairwise distance (e.g., Hamming distance) between the specific attribute from the query and the individual encoded attributes from the set of attributes determined from the EHRs. In embodiments, the system may compare the distance between the specific encounter attribute and each of the set of encounter attributes to a distance threshold. The distance threshold may be any type of threshold value or range (e.g., range between 0-1, minimum value, maximum value, etc.). For example, the system may return only hash values for attributes that have a computed distance that are less the 0.2 from the specific attribute provided in the request. Once the distances between the specific attribute and the set of attributes are computed and compared, the system will retrieve only the one or more similar encounter attributes that meet the distance threshold.

In some embodiments, the system may output the retrieved one or more similar attributes to a user. For example, the one or more similar attributes may be sent to the remote device 102 in response to the query. In some embodiments, the retrieved one or more similar attributes sent by be classified by type (e.g., encounter, modality, inter-level aggregation, intra-level aggregation) when sent to the user.

Figure 4A:
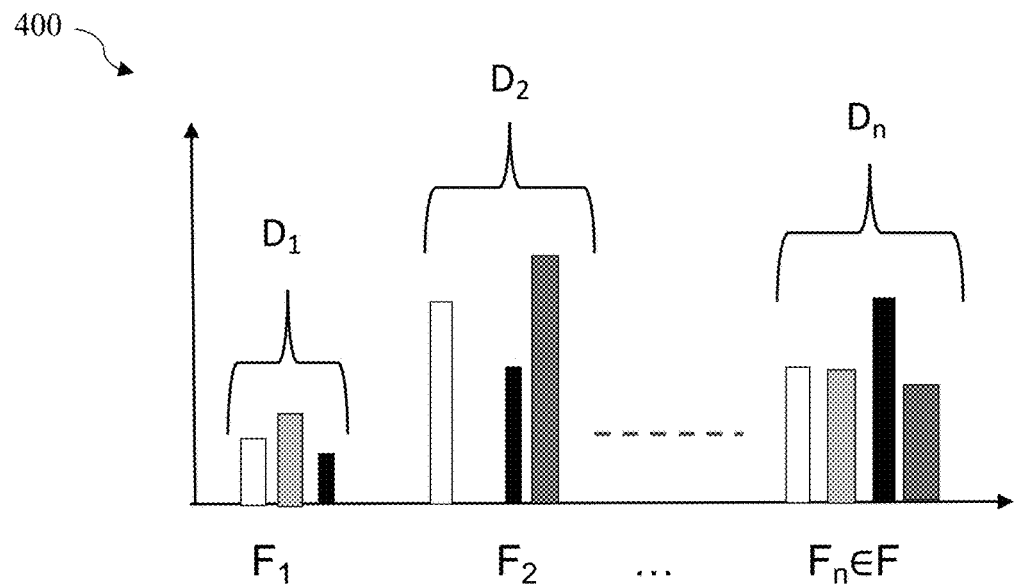
FIG. 4A illustrates an example graph detailing extracted features from electronic health records, in accordance with embodiments of the present disclosure.

Referring now to FIG. 4A, shown is an example graph 400 detailing extracted features from electronic health records, in accordance with embodiments of the present disclosure. In the illustrated embodiment, the various features (attributes) indicated by $F_1, F_2, \ldots F_n \in F$ are extracted from each encounter indicated by $D_1, D_2$, and $D_n$ that was collected from the EHRs. For example, the various features may include various measurement, symptoms, vitals, diagnoses, and/or demographics extracted from each encounter for a given patient. The system may perform an aggregated hashing function that classifies each encounter $D_1, D_2, D_n$ based on an aggregate set of specific features as shown in FIG. 4B.

Figure 4B:
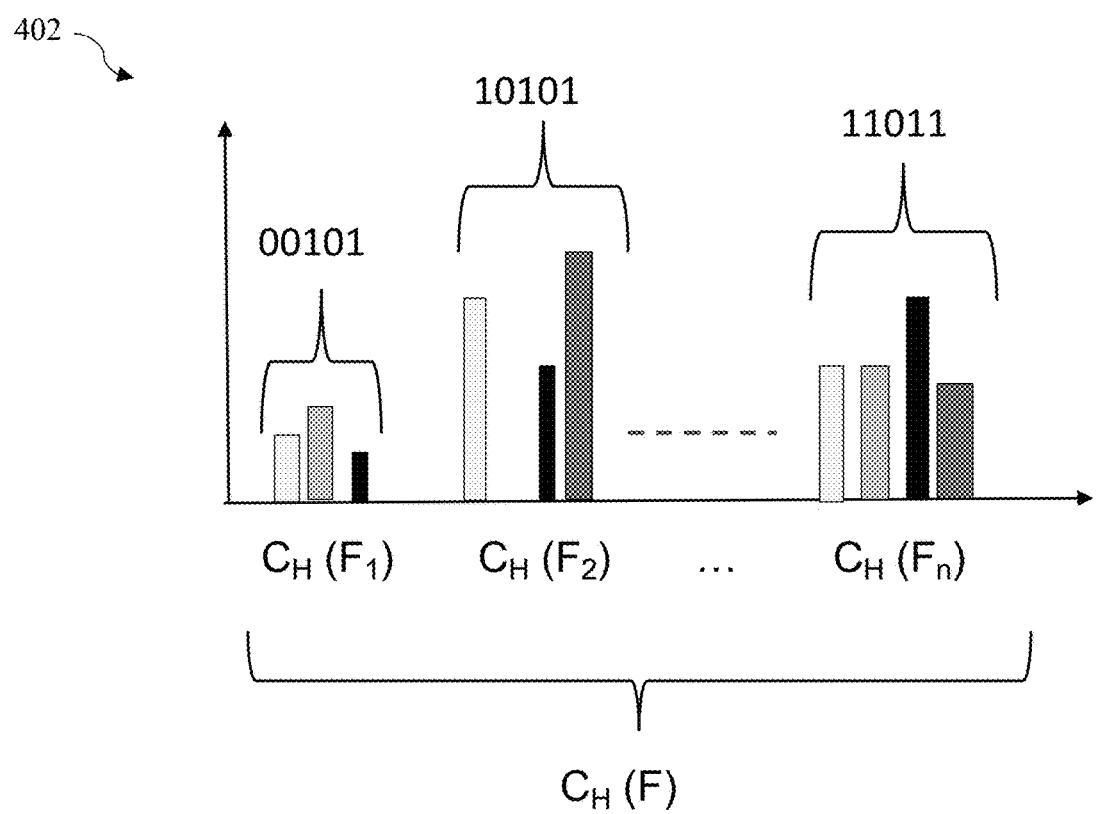
FIG. 4B illustrates an example graph detailing aggregated hashing of features extracted from electronic health records, in accordance with embodiments of the present disclosure.

Referring now to FIG. 4B, shown is an example graph 402 detailing aggregated hashing of features extracted from electronic health records, in accordance with embodiments of the present disclosure. In the illustrated embodiment, the aggregate hashing function $C_H$ (F) is performed to encode each aggregate set of specific features $C_H$ ($F_1$), $C_H$ ($F_2$), ... $C_H$ ($F_n$) of the given encounter with an aggregate hash value (e.g., 00101, 10101, and 11011). The aggregate hash value may be used to quickly identify and retrieve a given encounter when searching for similar encounters or features for a request/query as described in FIG. 3.

Figure 5A:
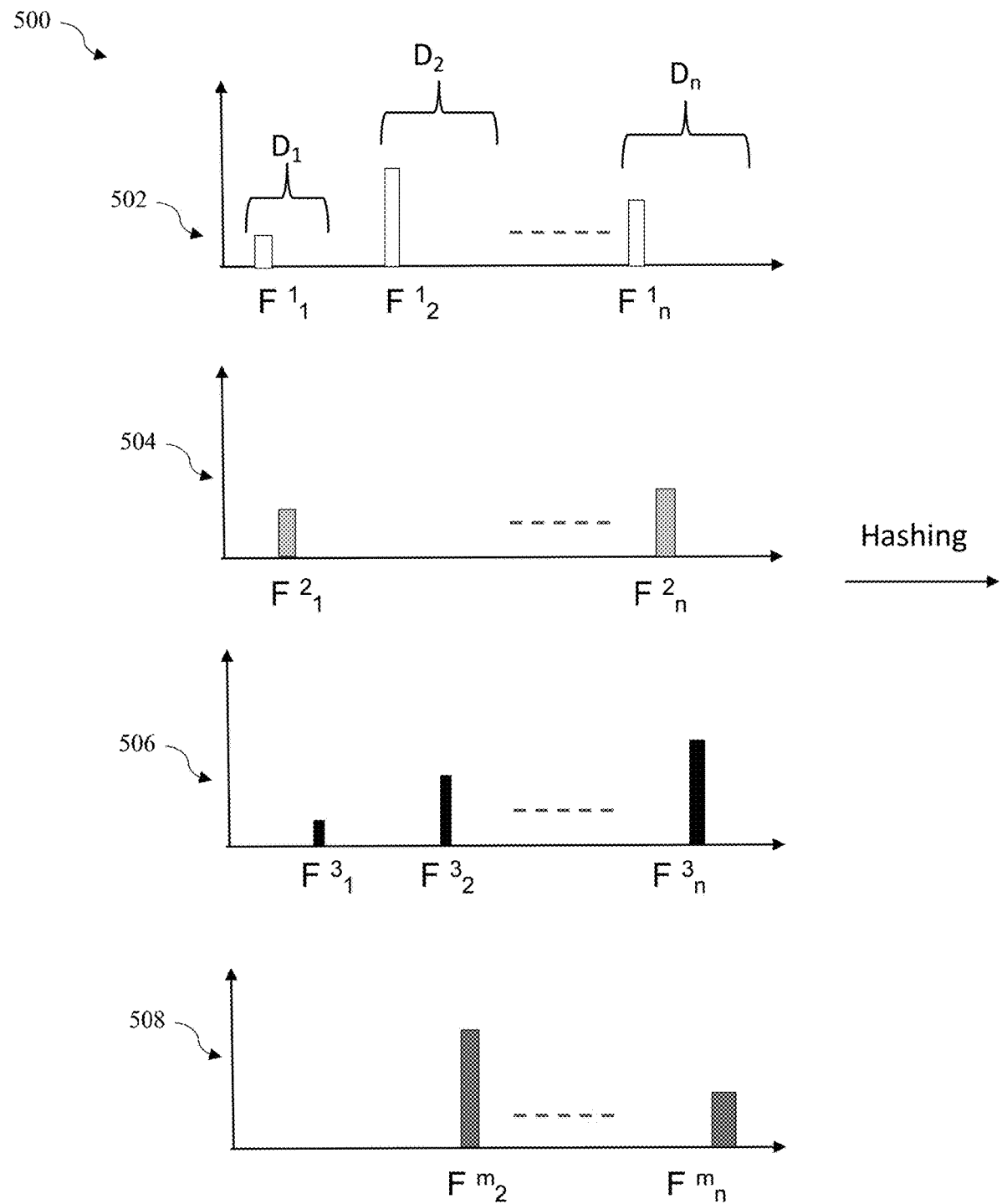
FIG. 5A illustrates a set of graphs detailing extracted features from electronic health records, in accordance with embodiments of the present disclosure.

Referring now to FIG. 5A, shown is a set of graphs 500 detailing extracted features from electronic health records, in accordance with embodiments of the present disclosure. In the illustrated embodiment, the set of graphs 500 correspond to the encounters indicated by $D_1, D_2$, and Dr, in graph 400 of FIG. 4A; however, the features are extracted and/or analyzed on an individual level rather than an aggregated level. For example, graph 502 shows extracted features $F^1_1, F^1_2, \ldots F^1n$ from each encounter $D_1, D_2$, and $D_n$, respectively; graph 504 show extracted features $F^2_1$ and $F^2_n$ from encounter $D_1$ and $D_n$, respectively; graph 506 shows extracted features $F^3_1, F^3_2$, and $F^3_n$ that from encounter $D_1$, $D_2$, and $D_n$, respectively; and graph 508 shows extracted features $F^m_2$ and $F^m_n$ from encounter $D_2$, and $D_n$, respectively. Once the features are separated on an individual level for each of the given encounters, the system may perform a feature-specific hashing function for each of the features as shown in FIG. 5B.

Figure 5B:
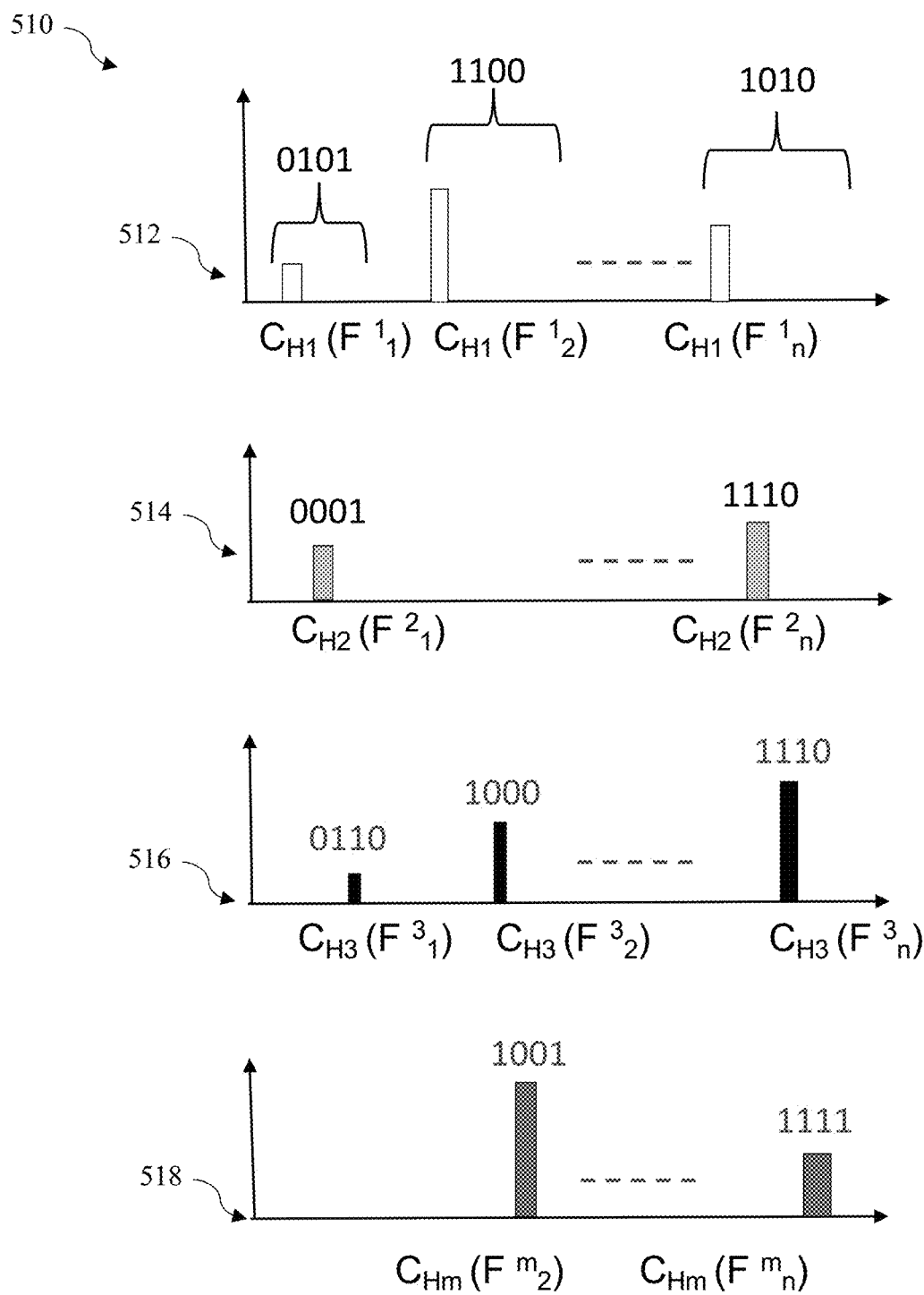
FIG. 5B illustrates a set of graphs detailing feature-specific hashing of extracted features from electronic health records, in accordance to embodiments of the present disclosure.

Referring now to FIG. 5B, shown is a set of graphs 510 detailing feature-specific hashing of extracted features from electronic health records, in accordance to embodiments of the present disclosure. In the illustrated embodiment, a feature-specific hashing function is performed to encode each respective feature with a specific hash value. For example, graph 512 shows hash functions $C_{H1}(F^1_1)$, $C_{H1}(F^1_2)$, and $C_{H1}(F^1_n)$ are used to generate hash values 0101, 1100, and 1010 for extracted features $F^1_1, F^1_2, \ldots F^1_n$, respectively; graph 514 shows hash functions $C_{H2}(F^2_1)$ and $C_{H2}(F^2_n)$ are used to generate hash values 0001 and 1110 for extracted features $F^2_1$ and $F^2_n$, respectively; graph 516 shows hash functions $C_{H3}(F^3_1)$, $C_{H3}(F^3_2)$, and $C_{H3}(F^3_n)$ are used to generate hash values 0110, 1000, and 1110 for extracted features $F^3_1, F^3_2$, and $F^3_n$, respectively; and graph 518 shows hash function $C_{Hm}(F^m_2)$ and $C_{Hm}(F^m_n)$ are used to generated hash values 1001 and 1111 for extracted features $F^m_2$ and $F^m_n$, respectively. In this way, the hashing values and/or hashing index may be used to identify specific features (or attributes) related to the EHRs on a more granular level (e.g., diagnosis, modality, etc.) by utilizing feature specific hash values.

Figure 6:
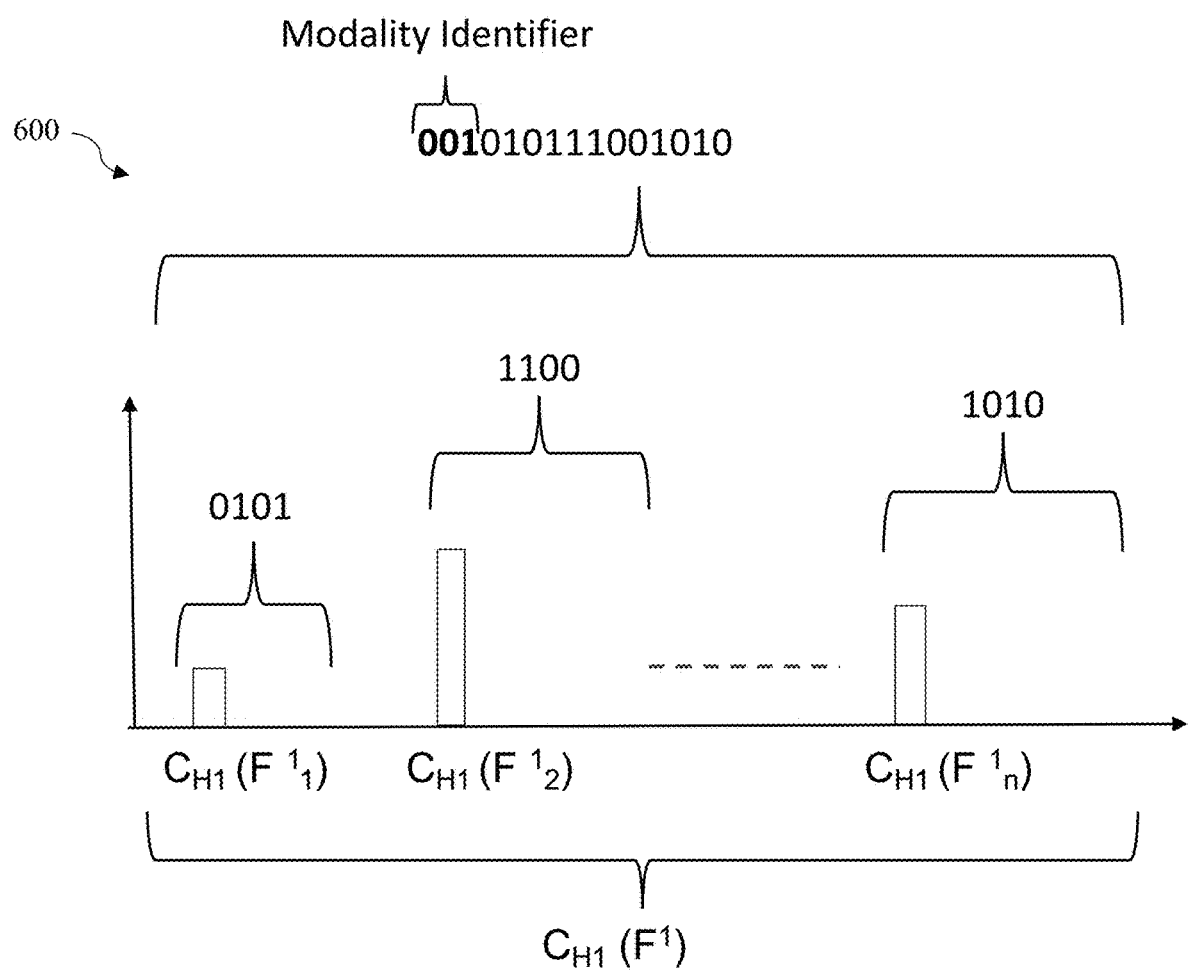
FIG. 6 illustrates an example graph for hashing electronic health records by using a modality identifier, in accordance to embodiments of the present disclosure.

Referring now to FIG. 6, shown is an example graph 600 for hashing electronic health records by using a modality identifier, in accordance to embodiments of the present disclosure. In the illustrated embodiment, the hash values may be assigned a modality identifier (001) that groups the one or more hash values (e.g., 0101, 1100, and 1010) related to a set of specific features by modality. The graph 600 as a whole may be identified by concatenating the modality identifier with each hash value found therein, resulting in a graph hash value of 001010111001010, as shown in FIG. 6. For example, an X-ray of a patient's lung may show one or more cancerous nodules. Using the modality identifier (001), the system may classify lung X-rays as the modality and the cancerous nodules as specific features. When performing a retrieval function using the hashing index, the system may quickly retrieve all lung X-rays of patients using the modality identifier. Further, the system may narrow down the search and retrieval function by limiting the modality to only provide lung X-rays that have the specific feature of a cancerous nodule. In this way, the system allows a user (e.g., doctor or healthcare provider) to quickly retrieve similar modalities or diagnosis from other EHRs that may aid in making decisions for a current patient's care.

Figure 7:
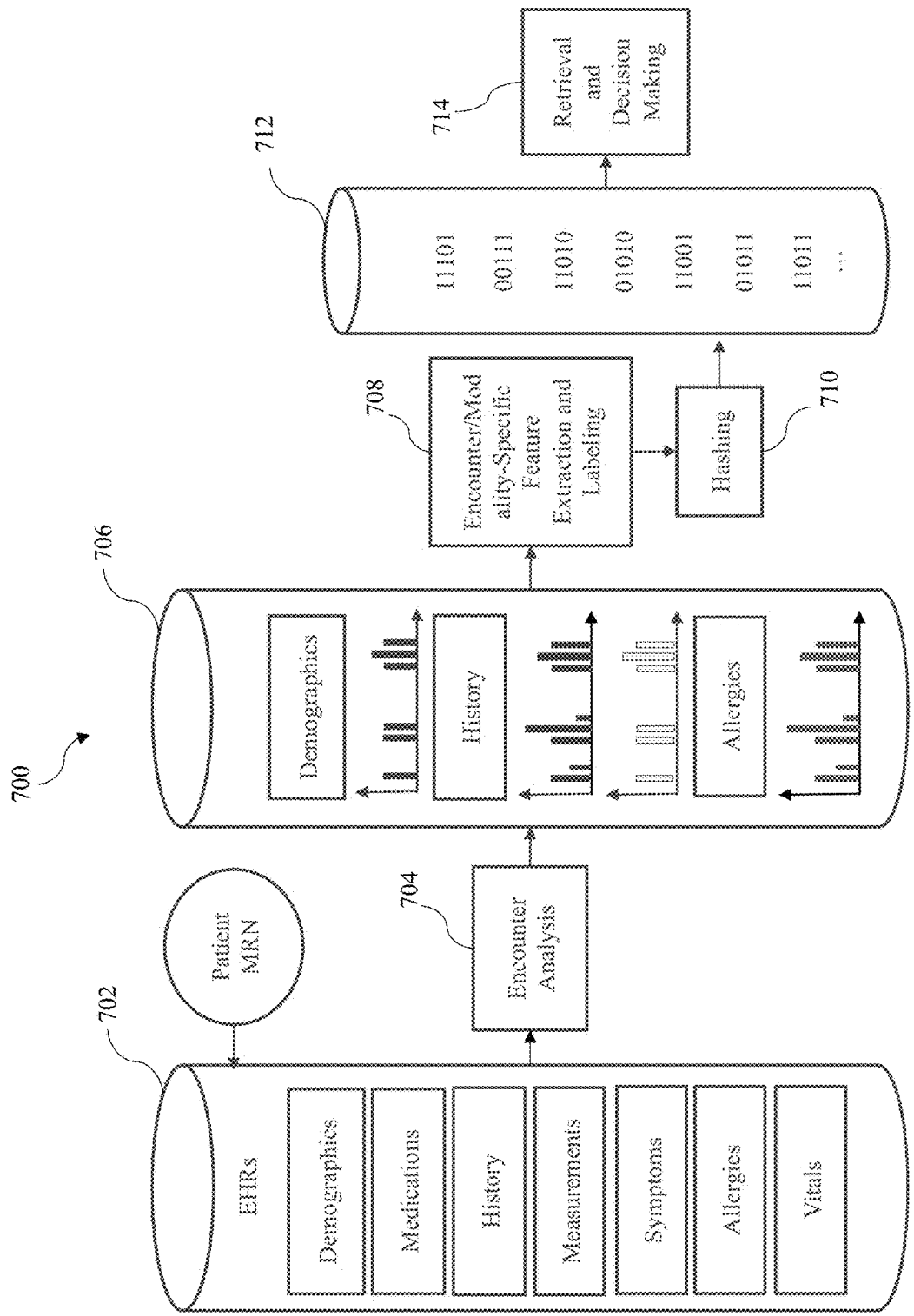
FIG. 7 illustrates an example block diagram showing steps for hashing electronic health records, in accordance to embodiments of the present disclosure.

Referring now to FIG. 7, shown is an example block diagram 700 showing steps for hashing electronic health records, in accordance with embodiments of the present disclosure. In the illustrated embodiment, a plurality of EHRs 702 are collected or obtained by the system (e.g., system 100 of FIG. 1). For example, and not meant to be limiting, the EHRs 702 may include various types of characteristics such as demographics, medications, history, measurements, symptoms, allergies, and/or vitals. The EHRs 702 may further include a medical records number (MRN) that corresponds to a patient such that various EHRs can be tracked/obtained related to the given patient or patients. In embodiments, the system may perform an encounter analysis 704 on each of the EHRs 702 to extract various features related to the given EHR. For example, the system may extract a set of features 706 (shown as histograms) for demographics, patient history, allergies, and the like.

In embodiments, the system may perform encounter/modality-specific feature extraction and labeling 708 that further extracts individual features from each of the set of features 706. Once the specific feature extraction and labeling 708 has been performed, the system may perform hashing 710 that generates hashing values 712 for each of the specific features that were extracted. Using the hashing values 712, the system may quickly retrieve 714 various health records that include any relevant features/characteristics and/or aspects that may aide a healthcare provider in making a patient care decision.

Figure 8:
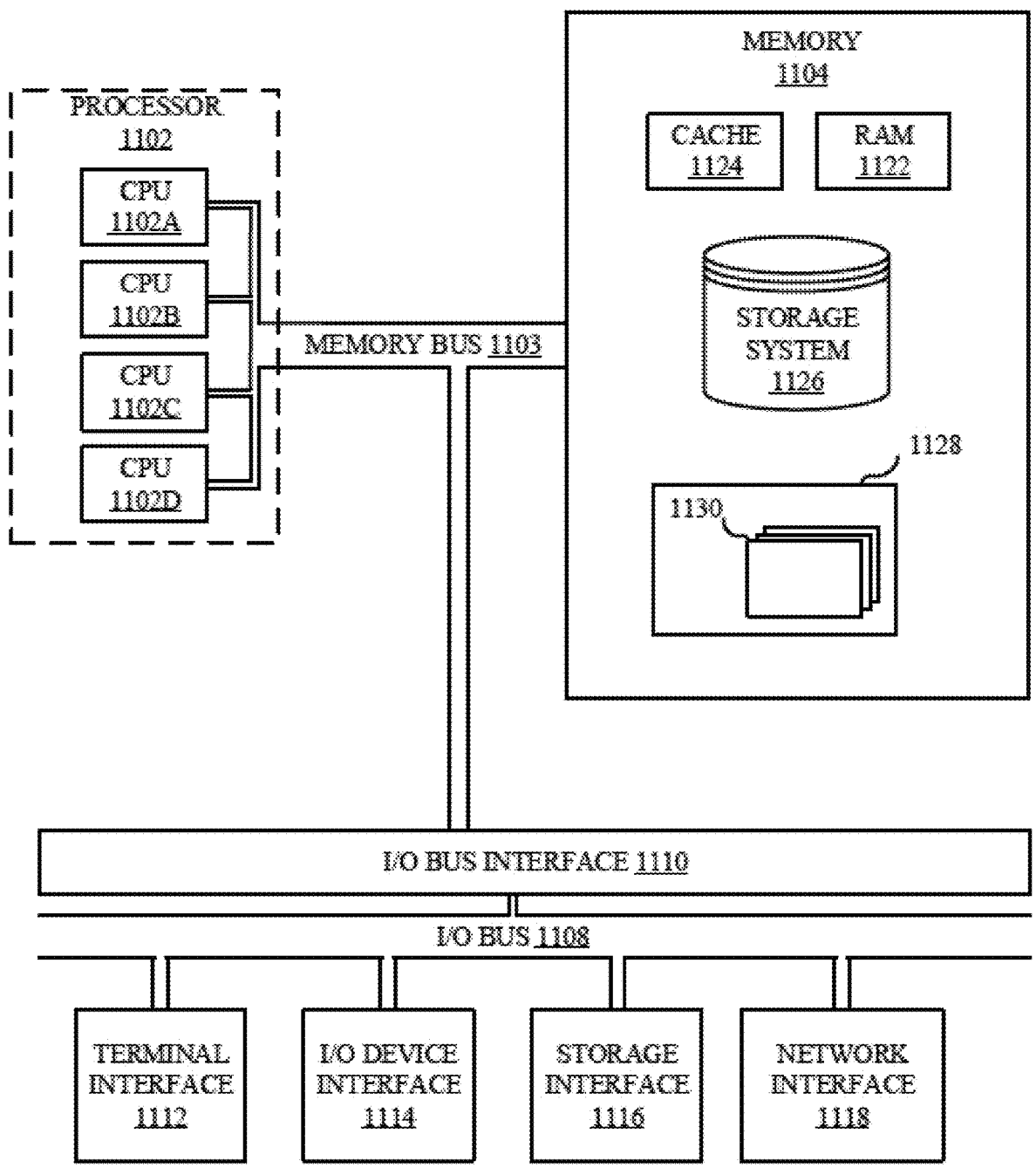
FIG. 8 illustrates a high-level block diagram of an example computer system that may be used in implementing one or more of the methods, tools, and modules, and any related functions, described herein, in accordance with embodiments of the present disclosure.

Referring now to FIG. 8, shown is a high-level block diagram of an example computer system 1101 that may be used in implementing one or more of the methods, tools, and modules, and any related functions, described herein (e.g., using one or more processor circuits or computer processors of the computer), in accordance with embodiments of the present disclosure. In some embodiments, the major components of the computer system 1101 may comprise one or more CPUs 1102, a memory subsystem 1104, a terminal interface 1112, a storage interface 1116, an I/O (Input/Output) device interface 1114, and a network interface 1118, all of which may be communicatively coupled, directly or indirectly, for inter-component communication via a memory bus 1103, an I/O bus 1108, and an I/O bus interface 1110.

The computer system 1101 may contain one or more general-purpose programmable central processing units (CPUs) 1102A, 1102B, 1102C, and 1102D, herein generically referred to as the CPU 1102. In some embodiments, the computer system 1101 may contain multiple processors typical of a relatively large system; however, in other embodiments the computer system 1101 may alternatively be a single CPU system. Each CPU 1102 may execute instructions stored in the memory subsystem 1104 and may include one or more levels of on-board cache. In some embodiments, a processor can include at least one or more of, a memory controller, and/or storage controller. In some embodiments, the CPU can execute the processes included herein (e.g., process 300 and 500).

System memory subsystem 1104 may include computer system readable media in the form of volatile memory, such as random-access memory (RAM) 1122 or cache memory 1124. Computer system 1101 may further include other removable/non-removable, volatile/non-volatile computer system data storage media. By way of example only, storage system 1126 can be provided for reading from and writing to a non-removable, non-volatile magnetic media, such as a "hard drive." Although not shown, a magnetic disk drive for reading from and writing to a removable, non-volatile magnetic disk (e.g., a "floppy disk"), or an optical disk drive for reading from or writing to a removable, non-volatile optical disc such as a CD-ROM, DVD-ROM or other optical media can be provided. In addition, memory subsystem 1104 can include flash memory, e.g., a flash memory stick drive or a flash drive. Memory devices can be connected to memory bus 1103 by one or more data media interfaces. The memory subsystem 1104 may include at least one program product having a set (e.g., at least one) of program modules that are configured to carry out the functions of various embodiments.

Although the memory bus 1103 is shown in FIG. 8 as a single bus structure providing a direct communication path among the CPUs 1102, the memory subsystem 1104, and the I/O bus interface 1110, the memory bus 1103 may, in some embodiments, include multiple different buses or communication paths, which may be arranged in any of various forms, such as point-to-point links in hierarchical, star or web configurations, multiple hierarchical buses, parallel and redundant paths, or any other appropriate type of configuration. Furthermore, while the I/O bus interface 1110 and the I/O bus 1108 are shown as single units, the computer system 1101 may, in some embodiments, contain multiple I/O bus interfaces 1110, multiple I/O buses 1108, or both. Further, while multiple I/O interface units are shown, which separate the I/O bus 1108 from various communications paths running to the various I/O devices, in other embodiments some or all of the I/O devices may be connected directly to one or more system I/O buses.

In some embodiments, the computer system 1101 may be a multi-user mainframe computer system, a single-user system, or a server computer or similar device that has little or no direct user interface, but receives requests from other computer systems (clients). Further, in some embodiments, the computer system 1101 may be implemented as a desktop computer, portable computer, laptop or notebook computer, tablet computer, pocket computer, telephone, smart phone, network switches or routers, or any other appropriate type of electronic device.

It is noted that FIG. 8 is intended to depict the representative major components of an exemplary computer system 1101. In some embodiments, however, individual components may have greater or lesser complexity than as represented in FIG. 8, components other than or in addition to those shown in FIG. 8 may be present, and the number, type, and configuration of such components may vary.

One or more programs/utilities 1128, each having at least one set of program modules 1130 may be stored in memory subsystem 1104. The programs/utilities 1128 may include a hypervisor (also referred to as a virtual machine monitor), one or more operating systems, one or more application programs, other program modules, and program data. Each of the operating systems, one or more application programs, other program modules, and program data or some combination thereof, may include an implementation of a networking environment. Programs/utilities 1128 and/or program modules 1130 generally perform the functions or methodologies of various embodiments.

It is understood in advance that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 9:
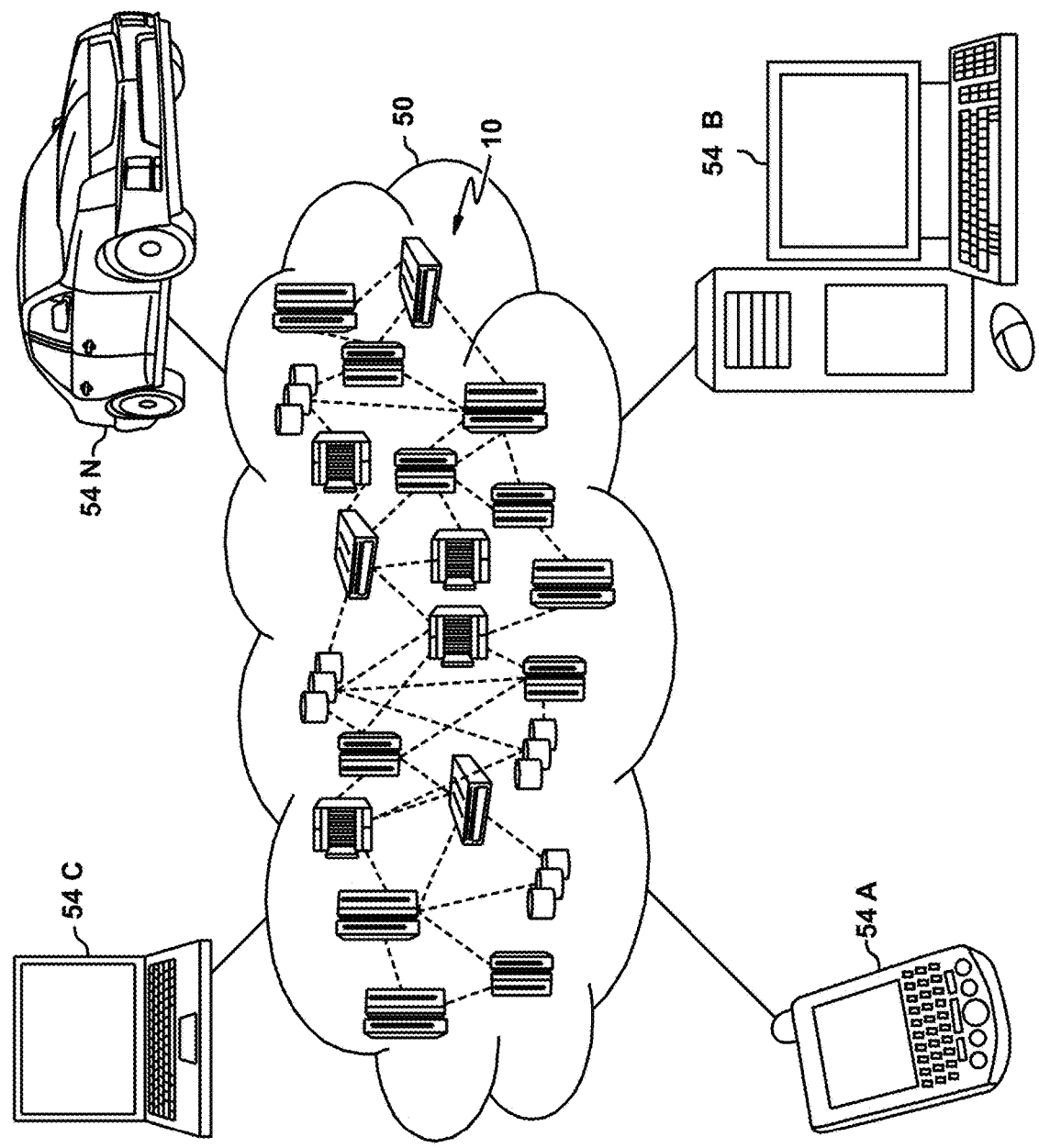
FIG. 9 depicts a cloud computing environment in accordance with embodiments of the present disclosure.

Referring now to FIG. 9, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 9 are intended to be illustrative only and that computing nodes 10 and cloud computing environment 50 can communicate with any type of computerized device over any type of network and/or network addressable connection (e.g., using a web browser).

Figure 10:
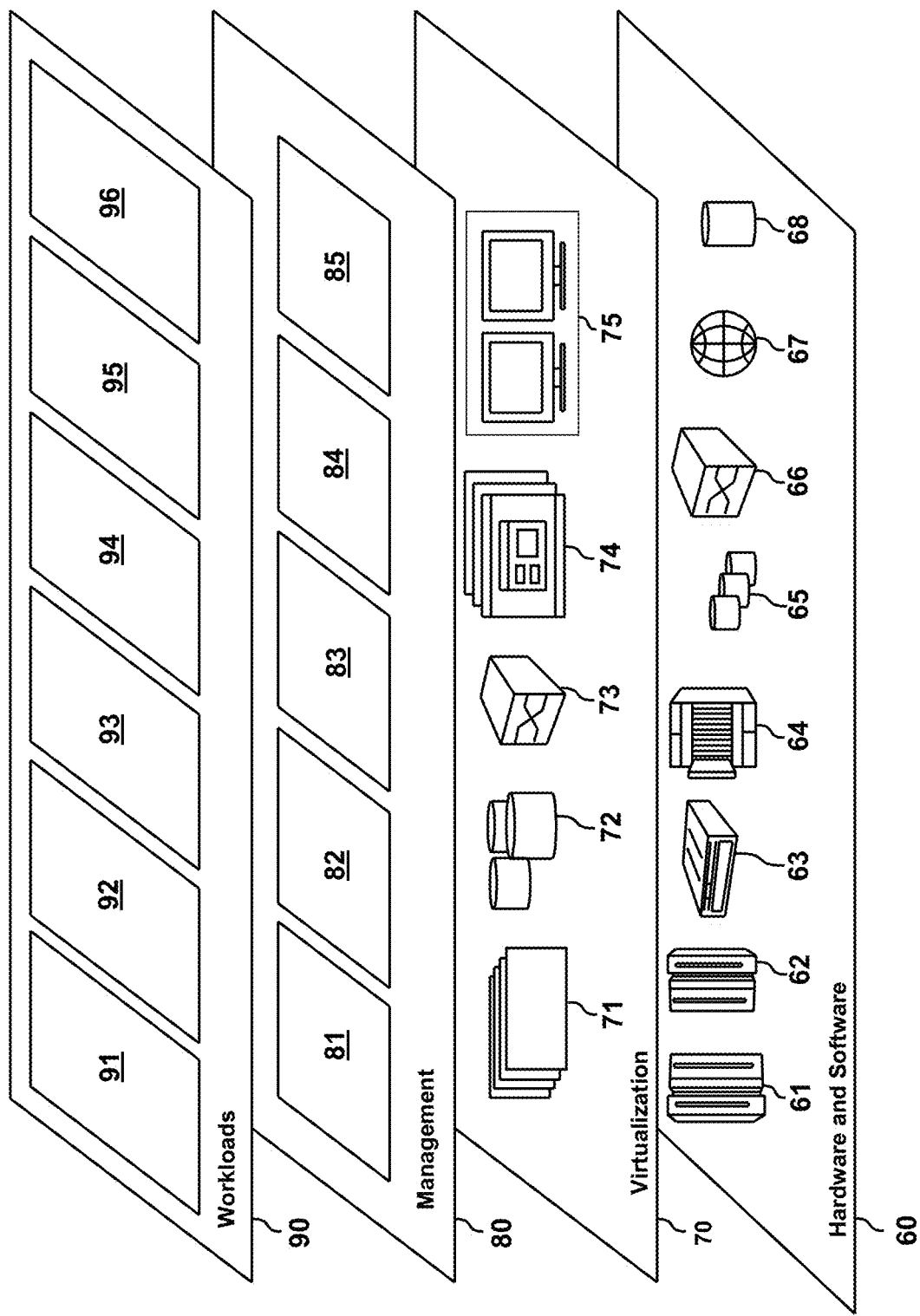
FIG. 10 depicts abstraction model layers in accordance with embodiments of the present disclosure.

Referring now to FIG. 10, a set of functional abstraction layers provided by cloud computing environment 50 (FIG. 9) is shown. It should be understood in advance that the components, layers, and functions shown in FIG. 10 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and hashing engine software 68 in relation to the hashing engine 126 of host device 112 illustrated in FIG. 1.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and mobile desktops 96.

As discussed in more detail herein, it is contemplated that some or all of the operations of some of the embodiments of methods described herein may be performed in alternative orders or may not be performed at all; furthermore, multiple operations may occur at the same time or as an internal part of a larger process.

The present invention may be a system, a method, and/or a computer program product at any possible technical detail level of integration. The computer program product may include a computer readable storage medium (or media) having computer readable program instructions thereon for causing a processor to carry out attributes of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform attributes of the present invention.

Attributes of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement attributes of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the various embodiments. As used herein, the singular forms "a," "an," and "the" are intended to include the plural forms as well, unless the context clearly indicates otherwise. It will be further understood that the terms "includes" and/or "including," when used in this specification, specify the presence of the stated features, integers, steps, operations, elements, and/or components, but do not preclude the presence or addition of one or more other features, integers, steps, operations, elements, components, and/or groups thereof. In the previous detailed description of example embodiments of the various embodiments, reference was made to the accompanying drawings (where like numbers represent like elements), which form a part hereof, and in which is shown by way of illustration specific example embodiments in which the various embodiments may be practiced. These embodiments were described in sufficient detail to enable those skilled in the art to practice the embodiments, but other embodiments may be used and logical, mechanical, electrical, and other changes may be made without departing from the scope of the various embodiments. In the previous description, numerous specific details were set forth to provide a thorough understanding the various embodiments. But, the various embodiments may be practiced without these specific details. In other instances, well-known circuits, structures, and techniques have not been shown in detail in order not to obscure embodiments.

As used herein, "a number of" when used with reference to items, means one or more items. For example, "a number of different types of networks" is one or more different types of networks.

When different reference numbers comprise a common number followed by differing letters (e.g., 100a, 100b, 100c) or punctuation followed by differing numbers (e.g., 100-1, 100-2, or 100.1, 100.2), use of the reference character only without the letter or following numbers (e.g., 100) may refer to the group of elements as a whole, any subset of the group, or an example specimen of the group.

Further, the phrase "at least one of," when used with a list of items, means different combinations of one or more of the listed items can be used, and only one of each item in the list may be needed. In other words, "at least one of" means any combination of items and number of items may be used from the list, but not all of the items in the list are required. The item can be a particular object, a thing, or a category.

For example, without limitation, "at least one of item A, item B, or item C" may include item A, item A and item B, or item B. This example also may include item A, item B, and item C or item B and item C. Of course, any combinations of these items can be present. In some illustrative examples, "at least one of" can be, for example, without limitation, two of item A; one of item B; and ten of item C; four of item B and seven of item C; or other suitable combinations.

Different instances of the word "embodiment" as used within this specification do not necessarily refer to the same embodiment, but they may. Any data and data structures illustrated or described herein are examples only, and in other embodiments, different amounts of data, types of data, fields, numbers and types of fields, field names, numbers and types of rows, records, entries, or organizations of data may be used. In addition, any data may be combined with logic, so that a separate data structure may not be necessary. The previous detailed description is, therefore, not to be taken in a limiting sense.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Although the present invention has been described in terms of specific embodiments, it is anticipated that alterations and modification thereof will become apparent to the skilled in the art. Therefore, it is intended that the following claims be interpreted as covering all such alterations and modifications as fall within the true spirit and scope of the invention.

What is claimed is:

1. A computer-implemented method comprising:
    collecting a set of electronic health records (EHRs) comprising one or more EHRs;
    performing an encounter analysis on the set of EHRs to determine a set of attributes associated to the set of EHRs, wherein the encounter analysis comprises, for each EHR:
        executing data analysis on the EHR, wherein results of the data analysis identifies a portion of the EHR corresponding to an encounter, and identifies one or more encounter attributes recorded in the EHR for the encounter, wherein the encounter represents a consultation or visit between a patient corresponding to the EHR and a healthcare provider, and wherein the one or more encounter attributes are attributes in the set of attributes; and
        classifying each encounter attribute, in the one or more corresponding encounter attributes, according to a plurality of attribute types and associating each encounter attribute with a corresponding attribute type;
    hashing the set of attributes to generate one or more hashing indexes that correspond to the set of EHRs, wherein generating the one or more hashing indexes comprises:
        generating a separate hash value for each encounter in the set of EHRs based on an application of a hash function to corresponding encounter attributes;
        combining the separate hash values to generate a combined hash value; and
        concatenating a classification type identifier to the combined hash value, wherein the classification type identifier indicates an attribute type associated with at least one attribute in the set of attributes;
    storing the one or more hashing indexes in a list used for document retrieval;
    receiving a request to retrieve one or more similar attributes that match a specific attribute; and
    retrieving the one or more similar attributes using the one or more hashing indexes at least by retrieving combined hash values having a classification type identifier specifying an attribute type corresponding to a type indicated by the request, and comparing hash values in the retrieved combined hash values to a hash value of a request attribute corresponding to the request.

2. The computer-implemented method of claim 1, further comprising:
outputting the retrieved one or more similar attributes by a type selected from the group consisting of:
encounter;
modality;
inter-level aggregation; and
intra-level aggregation.

3. The computer-implemented method of claim 1, wherein retrieving the one or more similar attributes using the one or more hashing indexes comprises:
computing a distance between the specific attribute and each of the set of attributes from the one or more hashing indexes;
comparing the distance between the specific attribute and each of the set of attributes to a distance threshold; and
retrieving the one or more similar attributes that meet the distance threshold.

4. The computer-implemented method of claim 1, wherein the plurality of attribute types comprise at least one of an encounter type, a modality type, a clinical outcome type, a demographic type, a symptom type, a location type, and a medication type, and wherein the classification type identifier is an identifier specifying the particular attribute type.

5. The computer-implemented method of claim 1, wherein the classification type identifier is an International Classification of Diseases (ICD) code corresponding to a corresponding attribute type.

6. The computer-implemented method of claim 1, wherein the data analysis comprises at least one of natural language processing on unstructured text associated with the set of EHRs, or image analysis on images associated with the set of EHRs to extract image features from the images.

7. The computer-implemented method of claim 1, wherein, for at least one hashing index, in the one or more hashing indexes, the classification type identifier identifies an imaging modality used to capture medical images during each encounter whose encounter attributes are represented in the at least one hashing index.

8. A system comprising:
a processor; and
a computer-readable storage medium communicatively coupled to the processor and storing program instructions which, when executed by the processor, cause the processor to perform a method comprising:
collecting a set of electronic health records (EHRs) comprising one or more EHRs;
performing an encounter analysis on the set of EHRs to determine a set of attributes associated to the set of EHRs, wherein the encounter analysis comprises, for each EHR:
executing data analysis on the EHR, wherein results of the data analysis identifies a portion of the EHR corresponding to an encounter, and identifies one or more encounter attributes recorded in the EHR for the encounter, wherein the encounter represents a consultation or visit between a patient corresponding to the EHR and a healthcare provider, and wherein the one or more encounter attributes are attributes in the set of attributes; and
classifying each encounter attribute, in the one or more corresponding encounter attributes, according to a plurality of attribute types and associating each encounter attribute with a corresponding attribute type;
hashing the set of attributes to generate one or more hashing indexes that correspond to the set of EHRs, wherein generating the one or more hashing indexes comprises:
generating a separate hash value for each encounter in the set of EHRs based on an application of a hash function to corresponding encounter attributes;
combining the separate hash values to generate a combined hash value; and
concatenating a classification type identifier to the combined hash value, wherein the classification type identifier indicates an attribute type associated with at least one attribute in the set of attributes;
storing the one or more hashing indexes in a list used for document retrieval;
receiving a request to retrieve one or more similar attributes that match a specific attribute; and
retrieving the one or more similar attributes using the one or more hashing indexes at least by retrieving combined hash values having a classification type identifier specifying an attribute type corresponding to a type indicated by the request, and comparing hash values in the retrieved combined hash values to a hash value of a request attribute corresponding to the request.

9. The system of claim 8, wherein the method performed by the processor further comprises:
outputting the retrieved one or more similar attributes by a type selected from the group consisting of:
an encounter;
a modality;
an inter-level aggregation; and
an intra-level aggregation.

10. The system of claim 8, wherein retrieving the one or more similar attributes using the one or more hashing indexes comprises:
computing a distance between the specific attribute and each of the set of attributes from the one or more hashing indexes;
comparing the distance between the specific attribute and each of the set of attributes to a distance threshold; and
retrieving the one or more similar attributes that meet the distance threshold.

11. The system of claim 8, wherein the classification type identifier is an International Classification of Diseases (ICD) code corresponding to a corresponding attribute type.

12. The system of claim 8, wherein the plurality of attribute types comprise at least one of an encounter type, a modality type, a clinical outcome type, a demographic type, a symptom type, a treatment type, a location type, and a medication type, and wherein the classification type identifier is an identifier specifying the particular attribute type.

13. The system of claim 8, wherein, for at least one hashing index, in the one or more hashing indexes, the classification type identifier identifies an imaging modality used to capture medical images during each encounter whose encounter attributes are represented in the at least one hashing index.

14. A computer program product comprising a computer-readable storage medium having program instructions embodied therewith, the program instructions executable by a processor to cause the processor to perform a method comprising:
collecting a set of electronic health records (EHRs) comprising one or more EHRs;

performing an encounter analysis on the set of EHRs to determine a set of attributes associated to the set of EHRs, wherein the encounter analysis comprises, for each EHR:
  executing data analysis on the EHR, wherein results of the data analysis identifies a portion of the EHR corresponding to an encounter, and identifies one or more encounter attributes recorded in the EHR for the encounter, wherein the encounter represents a consultation or visit between a patient corresponding to the EHR and a healthcare provider, and wherein the one or more encounter attributes are attributes in the set of attributes; and
  classifying each encounter attribute, in the one or more corresponding encounter attributes, according to a plurality of attribute types and associating each encounter attribute with a corresponding attribute type;
hashing the set of attributes to generate one or more hashing indexes that correspond to the set of EHRs, wherein generating the one or more hashing indexes comprises:
  generating a separate hash value for each encounter in the set of EHRs based on an application of a hash function to corresponding encounter attributes;
  combining the separate hash values to generate a combined hash value; and
  concatenating a classification type identifier to the combined hash value, wherein the classification type identifier indicates an attribute type associated with at least one attribute in the set of attributes;
storing the one or more hashing indexes in a list used for document retrieval;
receiving a request to retrieve one or more similar attributes that match a specific attribute; and
retrieving the one or more similar attributes using the one or more hashing indexes at least by retrieving combined hash values having a classification type identifier specifying an attribute type corresponding to a type indicated by the request, and comparing hash values in the retrieved combined hash values to a hash value of a request attribute corresponding to the request.

15. The computer program product of claim 6, wherein retrieving the one or more similar attributes using the one or more hashing indexes comprises:
  computing a distance between the specific attribute and each of the set of attributes from the one or more hashing indexes, wherein the distance is measured by a Hamming distance between hash values associated with the set of attributes and the specific attribute;
  comparing the distance between the specific attribute and each of the set of attributes to a distance threshold; and
  retrieving the one or more similar attributes that meet the distance threshold.

16. The computer program product of claim 14, wherein the method performed by the processor further comprises:
  outputting the retrieved one or more similar attributes by a type selected from the group consisting of:
  an encounter;
  a modality;
  an inter-level aggregation; and
  an intra-level aggregation.

17. The computer program product of claim 14, wherein, for at least one hashing index, in the one or more hashing indexes, the classification type identifier identifies an imaging modality used to capture medical images during each encounter whose encounter attributes are represented in the at least one hashing index.

* * * * *